United States Patent
Butler et al.

(10) Patent No.: US 6,486,371 B1
(45) Date of Patent: Nov. 26, 2002

(54) MULTISTAGE REACTION SYSTEM WITH INTERSTAGE SPARGER SYSTEMS

(75) Inventors: James R. Butler, Houston, TX (US); Denis Mignon, Braine-l'Alleud (BE)

(73) Assignee: Fina Technology, Inc., Houston, TX (US)

( * ) Notice: Subject to any disclaimer, the term of this patent is extended or adjusted under 35 U.S.C. 154(b) by 0 days.

(21) Appl. No.: 09/723,650

(22) Filed: Nov. 28, 2000

(51) Int. Cl.[7] .............................. C07C 2/66; B01J 8/04
(52) U.S. Cl. ..................... 585/449; 585/467; 585/921; 585/922; 422/190; 422/191; 422/194; 422/195; 422/207; 422/224; 422/225
(58) Field of Search ................ 585/467, 444, 585/421, 422; 422/190, 191, 194, 195, 207, 224, 225

(56) References Cited

U.S. PATENT DOCUMENTS

| | | |
|---|---|---|
| 3,478,119 A * | 11/1969 | Maier et al. ................ 585/448 |
| 3,728,249 A | 4/1973 | Antezana et al. ............. 208/57 |
| 4,107,224 A | 8/1978 | Dwyer ....................... 582/448 |
| 4,922,053 A | 5/1990 | Waguespack et al. ....... 585/447 |
| 5,847,255 A | 12/1998 | Ghosh et al. ............... 585/467 |

* cited by examiner

Primary Examiner—Thuan D. Dang
(74) Attorney, Agent, or Firm—William D. Jackson (57) ABSTRACT

Vapor phase alkylation of an aromatic substrate in a multi-stage alkylation reaction zone having a plurality of series-connected catalyst beds providing mixing zones between adjacent catalyst beds. An aromatic substrate and a $C_2$–$C_4$ alkylating agent is supplied to an inlet side of a gas phase reaction zone causing vapor phase alkylation of the aromatic substrate as the aromatic substrate and the alkylating agent flow through the reaction zone from one catalyst bed to the next. A quench fluid comprising one or both of the aromatic substrate and the alkylating agent is supplied into the interior of the mixing zone through a plurality of flow paths. One portion of the flow paths is directed upwardly and another portion downwardly within the mixing zone. The quench fluid is supplied to the mixing zone through a plurality of dispersion channels spaced laterally from one another.

16 Claims, 4 Drawing Sheets

MULTISTAGE REACTION SYSTEM WITH INTERSTAGE SPARGER SYSTEMS

FIELD OF THE INVENTION

This invention relates to a multi-stage hydrocarbon treatment process with interstate injection of a quenching fluid and more particularly to vapor phase alkylation of an aromatic substrate with an alkylating agent with interstage injection of a quenching fluid comprising at least one of the aromatic alkylating agent and the aromatic substrate.

BACKGROUND OF THE INVENTION

Hydrocarbon treatment processes in which a hydrocarbon reaction component is reacted with a second reaction component which may be a hydrocarbon or a non-hydrocarbon are well known in the chemical processing industry. An important aspect of such processes are aromatic conversion processes which are carried out over molecular sieve catalysts. Such aromatic conversion reactions include the alkylation of aromatic substrates such as benzene to produce alkyl aromatics such as ethylbenzene, ethyltoluene, cumene or higher aromatics and the transalkylation of polyalkyl benzenes to monoalkyl benzenes. Typically, an alkylation reactor which produces a mixture of mono- and poly- alkyl benzenes may be coupled through various separation stages to a downstream transalkylation reactor. Such alkylation and transalkylation conversion processes can be carried out in the liquid phase, in the vapor phase or under conditions in which both liquid and vapor phases are present.

Alkylation and transalkylation reactions may occur simultaneously within a single reactor. For example, where various series-connected catalyst beds are employed in an alkylation reactor as described below, it is a conventional practice to employ interstage injection of the aromatic substrate between the catalyst beds in order to control the temperature of the adiabatic process, which tends to enhance transalkylation reactions within the alkylation reactor. Without having cooling, the by-product (xylene) yield is too high. For example, in the ethylation of benzene with ethylene to produce ethylbenzene, the alkylation product within the reactor includes not only ethylbenzene but also polyethylbenzene, principally diethylbenzene with reduced amounts of triethylbenzene, as well as other alkylated aromatics such as cumene and butylbenzene. The interstage injection of the ethylene results not only further in alkylation reactions but also transalkylation reactions where, for example, benzene and diethylbenzene undergo transalkylation to produce ethylbenzene. Thus, even though a separate transalkylation reactor is connected downstream through a series of separation stages, it is the accepted practice to minimize polyalkylation within the alkylation reactor in order to facilitate the subsequent treatment and separation steps.

An example of vapor phase alkylation is found in U.S. Pat. No. 4,107,224 to Dwyer. Here, vapor phase ethylation of benzene over a zeolite catalyst is accomplished in a down flow reactor having four series-connected catalyst beds. The output from the reactor is passed to a separation system in which ethylbenzene product is recovered, with the recycle of polyethylbenzenes to the alkylation reactor where they undergo transalkylation reactions with benzene. The Dwyer catalysts are characterized in terms of those having a constraint index within the approximate range of 1–12 and include, with the constraint index in parenthesis, ZSM-5 (8.3), ZSM-11 (8.7), ZSM-12 (2), ZSM-35 (4.5), ZSM-38 (2), and similar materials.

U.S. Pat. No. 4,520,220 to Watson et al discloses the use of silicalite catalysts having an average crystal size of less than 8 microns and a silica/alumina ratio of at least about 200 in the ethylation of an aromatic substrate such as benzene or toluene to produce ethylbenzene or ethyltoluene, respectively. As disclosed in Watson et al, the alkylation procedure can be carried out in a multi-bed alkylation reactor at temperatures ranging from about 350°–500° C. and, more desirably, about 400°–475° C., with or without a steam co-feed. The reactor conditions in Watson et al are such as provide generally for vapor phase alkylation conditions.

Another procedure employing silicalite and involving the ethylation of benzene under vapor phase reaction conditions coupled with the recycle of polyethylbenzene containing products back to the alkylation reactor is disclosed in U.S. Pat. No. 4,922,053 to Wagnespack. Here, alkylation is carried out at temperatures generally in the range of 370° C. to about 470° C. and pressures ranging from atmospheric up to about 25 atmospheres over a catalyst such as silicalite or ZSM-5. The catalysts are described as being moisture sensitive and care is taken to prevent the presence of moisture in the reaction zone. The alkylation/transalkylation reactor comprises four series-connected catalyst beds. Benzene and ethylene are introduced into the top of the reactor to the first catalyst bed coupled by recycle of a polyethylbenzene fraction to the top of the first catalyst bed as well as the interstage injection of polyethylbenzene and benzene at different points in the reactor.

Another process involving the use of a silicalite as an alkylation catalyst involves the alkylation of an alkylbenzene substrate in order to produce dialkylbenzene of a suppressed ortho isomer content. Thus, as disclosed in U.S. Pat. No. 4,489,214 to Butler et al, silicalite is employed as a catalyst in the alkylation of a monoalkylated substrate, toluene or ethylbenzene, in order to produce the corresponding dialkylbenzene, such as ethyltoluene or diethylbenzene. Specifically disclosed in Butler et al is the ethylation of toluene to produce ethyltoluene under vapor phase conditions at temperatures ranging from 350°–500° C. As disclosed in Butler, the presence of ortho ethyltoluene in the reaction product is substantially less than the thermodynamic equilibrium amount at the vapor phase reaction conditions employed.

U.S. Pat. No. 5,847,255 to Ghosh et al discloses vapor phase alkylation with separate transalkylation in which the output from the transalkylation reactor is recycled to an intermediate separation zone. The Ghosh et al process employs a multi-stage alkylation reactor in which four or more series-connected catalyst beds are employed in a downflow vapor phase reactor. Both benzene and ethylene are applied to the inlet of the reactor along with interstage injection of ethylene and/or benzene between the catalyst stages. Here, a benzene separation zone, from which an ethylbenzene/polyethylbenzene fraction is recovered from the bottom with recycling of the overhead benzene fraction to the alkylation reactor, is preceded by a prefractionation zone. The prefractionation zone produces an overhead benzene fraction which is recycled along with the overheads from the benzene column and a bottom fraction which comprises benzene, ethylbenzene and polyethylbenzene. Two subsequent separation zones are interposed between the benzene separation zone and the transalkylation reactor to provide for recovery of ethylbenzene as the process product and a heavier residue fraction. The polyethylbenzene fraction from the last separation zone is applied to the transalkylation reactor and the output there is applied directly to the second benzene separation column or indirectly through a separator and then to the second benzene separation column. In Ghosh et al, the ratio of benzene (or other aromatics substrate) and alkylating agent can be varied along the length of the reactor with the introduction of one or both reactants into the reactor at locations between catalyst beds. Any suitable technique can be employed to accomplish the interstage introduction of reactants into the reactor, but a typical system comprises a sparger, comprising a header which supplies feed stock into a plurality of sparger tubes within the header.

SUMMARY OF THE INVENTION

In accordance with the present invention, there is provided a multi-stage hydrocarbon treatment process in a multi-stage reaction zone having a plurality of series-connected catalyst beds each containing a hydrocarbon reaction catalyst and spaced from one another to provide an intermediate mixing zone between adjacent catalyst beds. A processing feedstock containing a hydrocarbon substrate component and a normally gaseous-reacting component for reaction with said substrate component to produce a reaction product is supplied to the inlet side of the reaction zone. The reaction zone is operated under temperature and pressure conditions in which the hydrocarbon substrate component is in the gas phase to cause a gas phase reaction of the components to produce the desired reaction product in the presence of the catalyst. A quench fluid comprising at least one of the hydrocarbon substrate component and the reactant component is injected into at least one intermediate mixing zone between adjacent catalyst beds. This quench fluid is dispensed into the interior of the mixing zone through a plurality of flow paths in which one portion of the flow paths is directed upwardly within the mixing zone and another portion directed downwardly within the mixing zone. The reaction product produced by the reaction of the hydrocarbon substrate component and the reactant component is recovered from a down-stream outlet of the reaction zone.

In accordance with a preferred embodiment of the present invention, there is provided a process for the vapor phase alkylation of an aromatic substrate in a multi-stage alkylation reactor employing intermediate mixing zones. In carrying out the invention, there is provided a multi-stage reaction zone having a plurality of series-connected catalyst beds containing a molecular sieve aromatic alkylation catalyst. The catalyst beds are spaced from one another to provide mixing zones between adjacent catalyst beds. A feedstock containing an aromatic substrate and a $C_2$–$C_4$ alkylating agent is supplied to an inlet side of the reaction zone. The reaction zone is operated at temperature and pressure conditions in which the aromatic substrate is in the gas phase and causing vapor phase alkylation of the aromatic substrate as the aromatic substrate and the alkylating agent flow through the reaction zone and pass from one catalyst bed to the next. In at least one intermediate mixing zone between adjacent catalyst beds a quench fluid comprising one or both of the aromatic substrate and the alkylating agent is supplied into the interior of the mixing zone through a plurality of flow paths. In the flow paths, one portion of the flow paths is directed upwardly within the mixing zone and another portion downwardly within the mixing zone. Alkylated product is then recovered from the downstream side of the reaction zone. In a preferred embodiment of the invention, the aromatic substrate is benzene and the alkylating agent is an ethylating agent such as ethylene. In a further embodiment of the invention, the quench fluid is supplied to the mixing zone through a plurality of dispersion channels which are spaced laterally from one another and extend transversely across the mixing chamber. At least some of the dispersion channels dispense the quench fluid alternately, upwardly and downwardly within the mixing zone. Preferably, the dispersion channels are located within the upper one-half of the mixing zone.

In a further embodiment of the invention, a multi-stage alkylation reaction zone is provided within an elongated reactor having an upper catalyst bed extending transversely of the reactor and at least three subsequent catalyst beds extending transversely of the reactor and spaced from one another. Spacing between the catalyst beds provides an upper mixing zone between the first catalyst bed and the next adjacent catalyst bed and subsequent mixing zones between the succeeding catalyst beds. Sparger systems are provided in the mixing zones incorporating a plurality of laterally-spaced dispersion channels. A mixture of the aromatic substrate and the alkylating agent is supplied to the sparger systems to provide a plurality of flow paths through linearly-spaced orifice outlets in the dispersion channels directed upwardly and downwardly within the mixing zone.

In accordance with yet another aspect of the invention, there is provided an alkylation reactor comprising an elongated reactor vessel having an inlet for the supply of reactants and an outlet for the withdrawal of product from the vessel. A plurality of catalyst beds are provided along the length of the reactor with a plurality of sparger systems each comprising a plurality of laterally displaced dispersion tubes and a manifold or header connecting the spaced dispersion tubes to provide for the supply of feedstock there too. At least some of the dispersion tubes have openings along the lengths thereof in which the openings alternately open in a downward and an upward orientation to dispense feedstock into the mixing zones.

DETAILED DESCRIPTION OF THE INVENTION

The present invention follows the accepted practice of carrying out vapor phase alkylation of an aromatic substrate such as benzene in a reactor involving a plurality of series-connected catalyst stages with a supplementary injection of a quenching fluid or aromatic substrate and alkylating agent into mixing zones within the reactor interposed between reactor stages. Here, however, the interstage injection of the benzene or other aromatic substrate and ethylene or other alkylating agent is accomplished through the use of a unique sparging system in which the simultaneous flow of feedstock is directed both upwardly and downwardly within a mixing zone in a manner to enhance mixing of the reactants as they flow from one catalyst stage to the next.

Although the invention may be applied to the reaction in the vapor phase alkylation of any suitable aromatic substrate such as benzene or toluene with a $C_2$–$C_4$ alkylating agent to produce ethylbenzene, ethyltoluene, cumene, or heavier alkylated aromatic compounds, the invention shall be described in this detailed description with respect to the ethylation of benzene. Although various molecular sieve catalysts such as described above can be employed in such vapor phase alkylation reactions, a preferred molecular sieve catalyst is silicalite, and the following detailed description of the invention will be made with respect to the use of a silicalite alkylation catalyst.

Silicalite, as is well known in the art, is a molecular sieve catalyst which is similar to the ZSM-5 zeolites but is typically characterized by a higher silica/alumina ratio providing an aluminum unit cell ratio of less than 1 and, in addition, is normally characterized as having a somewhat larger than average crystal size than is commonly associated with the ZSM zeolites. As is well known in the art, silicalite, which in the as-synthesized form is characterized by orthorhombic symmetry, can be converted to monoclinic symmetry by a calcination procedure as disclosed, for example, in U.S. Pat. No. 4,599,473 to Debras et al. As described in detail in Debras et al, "Physico-chemical characterization of pentasil type materials, I. Precursors and calcined zeolites, and II. Thermal analysis of the precursors," ZEOLITES, 1985, Vol. 5, pp. 369–383, the silicalite typically has a relatively large crystal size. Thus, at an average of less than one aluminum atom per unit cell (a silica/alumina ratio of about 200) silicalite typically has an average crystal size of perhaps 5–10 microns or more. The aforementioned Pat. No. 4,489,214 to Butler et al discloses experimental work involving the ethylation of toluene over silicalite or a crystal size greater than one micron, ranging from 1–2 microns up to 8 microns. The silicalite is further characterized in terms of a variable aluminum gradient such that the aluminum gradient is positive when going from the interior to the surface of the molecular sieve crystal. That is, the silicalite can be characterized by a core portion which is relatively aluminum-deficient with an outer shell portion which is relatively aluminum-rich. It is to be understood that the term "aluminum-rich" is a relative term, and that for silicalite even the outer shell portion of the crystallite has a low aluminum content.

In a suitable system for application of the invention, the alkylation and transalkylation reactors are integrated with an intermediate recovery zone, preferably involving a plurality of separation zones operated in a manner to effectively provide feed streams to the reactors with recycle of the output from the transalkylation reactor to a benzene recovery zone downstream of the alkylation reactor. In this integrated mode of operation, the transalkylation product is applied to an initial stage of a benzene recovery zone. Subsequent separation steps are carried out in a manner to apply a split feed to the transalkylation reactor. The alkylation reactor is a multi-stage reaction zone containing at least three, and preferably four or more, series-connected catalyst beds which contain the silicalite or other molecular sieve alkylation catalyst. As described in greater detail below, the preferred silicalite alkylation catalyst preferably is silicalite characterized as having a high monoclinicity and a small sodium content. The preferred catalyst used in the transalkylation reactor is a molecular sieve having a pore size greater than the pore size of the silicalite catalyst. Preferably, the transalkylation catalyst is zeolite Y. As will be described in greater detail below, the alkylation reactor is preferably operated at substantially higher temperature conditions than the transalkylation reactor.

One application of the invention is in a system involving a multi-stage alkylation reactor with the output coupled to a four-stage separation system which in turn supplies a polyethylbenzene feed to a transalkylation reactor. In such an application, parallel alkylation and transalkylation reactors are employed. This results in a preferred mode of operation in which the parallel alkylation reactors are simultaneously operated in an alkylation mode while periodically one reactor can be taken off-stream with the feedstream completely supplied to the on-stream reactor. In the embodiment illustrated and described below, two parallel reactors are employed although it is to be recognized that three or more reactors can likewise be employed in parallel. A similar configuration is employed for the transalkylation reactors. The result is that simultaneous catalyst regeneration can occur in one reactor during operation of the remaining alkylation and/or transalkylation reactors. Assuming that two parallel reactors are employed, it can be seen that this mode of operation will, for the same flow rate of feedstream, result in the operation of the reactors at two different space velocities, with the space velocity during regeneration of a reactor being about twice that with both parallel reactors in operation.

Preferably, the alkylation reactor comprises at least four catalyst beds as described above. More beds can be provided, and it will sometimes be advantageous to provide at least five catalyst beds in the alkylation reactor. The reactor is operated so as to provide vapor phase alkylation (both the aromatic substrate and the alkylating agent are in the vapor phase) at temperatures ranging from about 630–800° F. at the inlet to about 700–850° F. at the outlet. The pressure may be within the range of about 250 to 450 psia with the pressure decreasing from one bed to the next as the temperature increases. By way of example, the benzene and ethylene supplied to the top of the reactor may enter the reactor at a temperature of about 740° F. and a pressure of about 430 psia. The alkylation reaction is exothermic so that the temperature progressively increases from the first to the last catalyst bed by a way of example. The interstage temperatures may increase from 750° F. for the first catalyst bed to 765° F. after the second catalyst bed to 820° F. after the third catalyst bed to a temperature of about 840° F. after the last catalyst bed.

Normally in the operation of multi-stage reaction zone of the type involved in the present invention, a benzene-ethylene mixture is introduced to the first catalyst bed at the top of the reaction zone and also in intermediate mixing zones between the several successive stages of catalyst beds. In the present invention, ethylene is supplied along with benzene to the top of the first catalyst bed top at the upper end of the reactor. In addition, interstage injection of ethylene and benzene in a quench feed is provided for between some or all of the subsequent catalyst beds. The benzene to ethylene mole ratio is about 15–25 as injected into the top of the alkylation reactor and progressively decreases because of the interstage injection of ethylene along with reduced amounts of benzene and coupled with the alkylation of the benzene to ethylbenzene and polyethylbenzenes.

The mole ratio of benzene to ethylene at the interstage injection points can vary from zero (no benzene injection) or about one up to about eight. The benzene can be employed in an amount less than the amount of ethylene on a mole basis. Stated otherwise, benzene can either not be injected between the catalyst beds or, if injected, can be employed in a relatively minor amount, i.e., a mole ratio of benzene to ethylene of less than one. On the other hand, the benzene/ ethylene mole ratio can be as high as eight, and at mixing zones near the outlet end of the reactor only benzene may be injected. This is coupled with a somewhat lower operating temperature than would normally be the case for vapor phase alkylation. The temperature of the benzene stream into the top of the alkylation reactor can be in the order of 720° F. or lower. The alkylation reaction is, of course, an exothermic reaction so that the temperature will increase progressively throughout the alkylation column as noted previously.

The silicalite alkylation catalyst employed in the present invention is a molecular sieve from the pentasil family of high silica molecular sieves. Such pentasil molecular sieves are described, for example, in Kokotailo et al, "Pentasil Family of High Silica Crystalline Materials," Chem. Soc. Special Publ. 33, 133–139 (1980).

The silicalite molecular sieve alkylation catalyst has a somewhat smaller pore size than the preferred zeolite-Y employed in the transalkylation reactor. The silicalite catalyst has an effective pore size or window within the range of 5–6 angstroms. Zeolite Y has a pore size of about 7 angstroms. The preferred silicalite catalyst has a somewhat smaller crystal size, less than one micron, than is usually the case. Preferably, the crystal size is even somewhat smaller, about 0.5 μm, as contrasted with a crystal size of perhaps 1–2 μm up to about 8 μm for similar catalysts such as disclosed in the aforementioned Pat. No. 4,489,214 to Butler et al.

A preferred silicalite for use in the present invention is extruded with an alumina binder in a "trilobe" shape having a nominal diameter of about $\frac{1}{16}$" and a length of the extrudate of about $\frac{1}{8}$–$\frac{1}{4}$". The "trilobe" cross-sectional shape is something of the order of a three-leaf clover. The purpose of this shape is to increase the surface area of the extruded catalyst beyond what one would expect with a normal cylindrical extrudate. The preferred silicalite catalyst is characterized as "monoclinic silicalite." Monoclinic silicalite may be prepared as disclosed in U.S. Pat. Nos. 4,781,906 to Cahen et al and 4,772,456 to DeClippeleir et al. Preferably, the catalysts will have near 100% monoclinicity although silicalite catalysts that are 70–80% monoclinic and about 20–30% orthorhombic symmetry may be used in the preferred embodiment of the invention. The silicalite preferably is present in an amount of 75–80 wt. % with the alumina binder being present in an amount of 20–25 wt. %. The silica/alumina ratio of the silicalite is at least 275 and preferably at least 300. An especially preferred silica/alumina ratio is 300–350, and silicalite within this range was used in experimental work respecting the invention as described hereafter. The silicalite may have an alpha value of about 20–30. The "alpha value" is characterized in terms of the activity of a catalyst for cracking hexane as disclosed in U.S. Pat. Nos. 4,284,529 to Shihabi and 4,559,314 to Shihabi. The catalyst typically contains small amounts of sodium and iron.

As noted previously, the silicalite alkylation catalyst has a crystal structure characterized by an aluminum-rich outer shell and an aluminum-deficient interior portion when compared with the outer shell. The silicalite catalyst is dry and has no appreciable or intended water content. The alumina binder is a high purity alumina such as "catapal alumina." The silicalite catalyst preferably contains only a small amount of sodium, about 70–200 ppm sodium oxide, and contains only a small amount of iron oxide, about 300–600 ppm. The catalyst need not contain any additional "promoter" metals incorporated during the synthesis of the catalyst.

Figure 1:
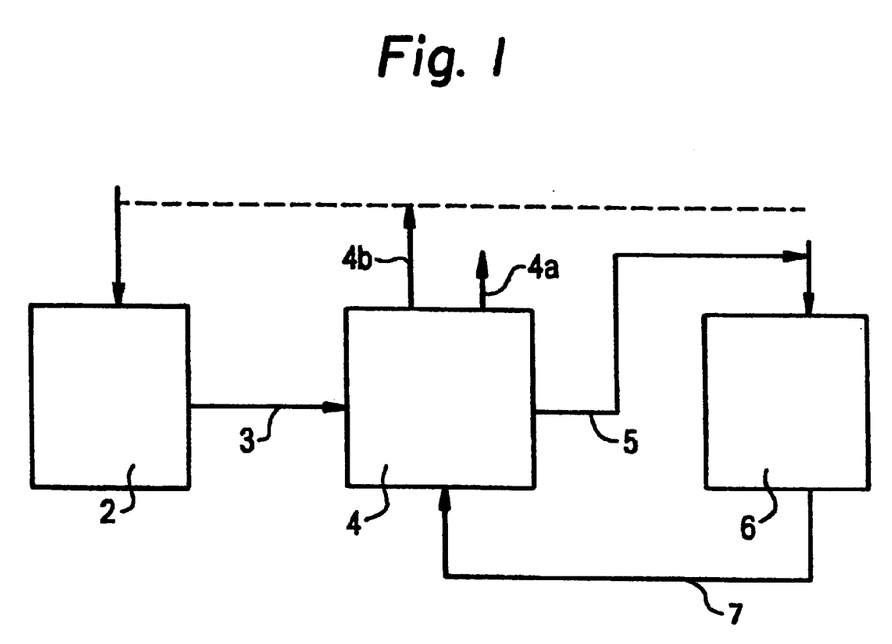
FIG. 1 is an idealized schematic block diagram of an alkylation/transalkylation process employing the present invention.

Turning now to the drawings and referring first to FIG. 1, there is illustrated a schematic block diagram of an alkylation/transalkylation process carried out in employing the present invention. As shown in FIG. 1, a product stream comprising a mixture of ethylene and benzene in a mole ratio of benzene to ethylene about 10 to 20 is supplied via line 1 to an alkylation zone 2. Alkylation zone 2 comprises one or more multi-stage reactors having a plurality of series-connected catalyst beds containing the silicalite as described above or another suitable molecular sieve alkylation catalyst. The alkylation zone is operated at temperature and pressure conditions to maintain the alkylation reaction in the vapor phase, i.e. the aromatic substrate is in the vapor phase and preferably at a feed rate to provide a space velocity enhancing diethylbenzene production while retarding xylene production.

The output from the alkylation reactor is supplied via line 3 to an intermediate recovery zone 4 which provides for the separation and recovery of ethylbenzene as a product. Thus, ethylbenzene is withdrawn from zone 4 via line 4a and applied for any suitable purposes such as in the production of vinylbenzene. Recovery zone 4 normally will be characterized by a plurality of series-connected distillation columns as described below and will result in a heavy polyalkylated product stream which is supplied via line 5 to a transalkylation zone 6. Typically, benzene will also be recovered from the intermediate recovery zone via a line 4b. The benzene may be applied as indicated by the broken lines both for recycle back to the alkylation reactor and also to the transalkylation zone as may be appropriate. Within the transalkylation zone, the benzene and diethylbenzene undergo a disproportionation reaction resulting in a product of enhanced ethylbenzene content and diminished benzene and diethylbenzene content. Typically, the output from the transalkylation zone will be supplied via line 7 for recycle to the separation zone 4.

Figure 2:
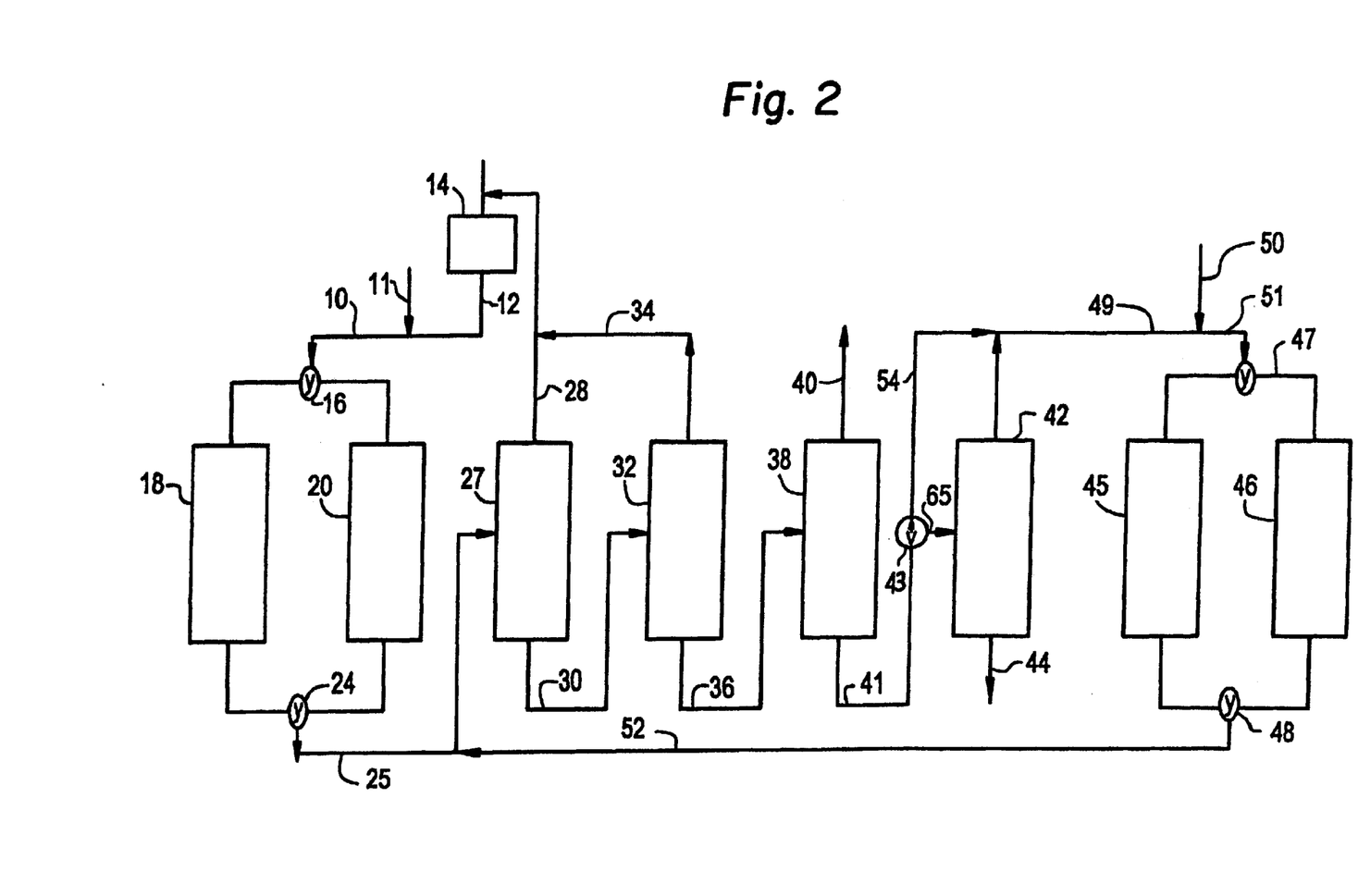
FIG. 2 is a schematic illustration of a process incorporating the present invention involving separate parallel-connected alkylation and transalkylation reactors with an intermediate multi-stage recovery zone for the separation and recycling of components.

Referring now to FIG. 2, there is illustrated in greater detail a suitable system incorporating a multi-stage intermediate recovery zone for the separation and recycling of components involved in the alkylation/transalkylation process. As shown in FIG. 2, an input feed stream is supplied by fresh ethylene through line 11 and fresh benzene through line 12. Line 12 is provided with a preheater 14 to heat the benzene stream to the desired temperature for the alkylation reaction. The feedstream is applied through a two-way, three-position valve 16 and inlet line 17 to the top of one or both parallel alkylation reaction zones 18 and 20 comprising a plurality of series connected catalyst beds each of which contains a molecular sieve alkylation catalyst. The reactors are operated at an average temperature, preferably within the range of 700° F.–800° F. and at pressure conditions of about 200 to 350 psia, to maintain the benzene in the gaseous phase.

In normal operation of the system depicted in FIG. 2, both reaction zones 18 and 20 will, during most of a cycle of operation, be operated in a parallel mode of operation in which they are both in service at the same time. In this case, valve 16 is configured so that the input stream in line 10 is roughly split to provide flow to both reactors in approximately equal amounts. 7. Periodically, one reactor can be taken off-stream for regeneration of the catalyst. Valve 16 is configured so that all of the feedstream from line 10 can be supplied to reactor 18 while the catalyst beds in reactor 20 are regenerated and visa versa. The regeneration procedure will be described in detail below but normally will take place over a relatively short period of time relative to the operation of the reactor in parallel alkylation mode. When regeneration of the catalyst beds in reactor 20 is completed, this reactor can then be returned on-stream, and at an appropriate point, the reactor 18 can be taken off-stream for regeneration. This results in a mode of operation of the individual catalyst beds at relatively lower space velocities for prolonged periods of time with periodic relatively short periods of operation at enhanced, relatively higher space velocities when one reactor is taken off-stream. By way of example, during normal operation of the system with both reactors 18 and 20 on-stream, the feedstream is supplied to each reactor to provide a space velocity of about 35 $hr^{-1}$ LHSV. When reactor 20 is taken off-stream and the feed rate continues unabated, the space velocity for reactor 18 will approximately double to 70 $hr^{-1}$ LHSV. When the regeneration of reactor 20 is completed, it is placed back on-stream, and again the flow rate space velocity for each reactor will decrease to 35 $hr^{-1}$ until such point as reactor 18 is taken off-stream, in which the case the flow rate to reactor 20 will, of course, increase, resulting again in a transient space velocity in reactor 20 of 70 $hr.^{-1}$ LHSV.

Figure 3:
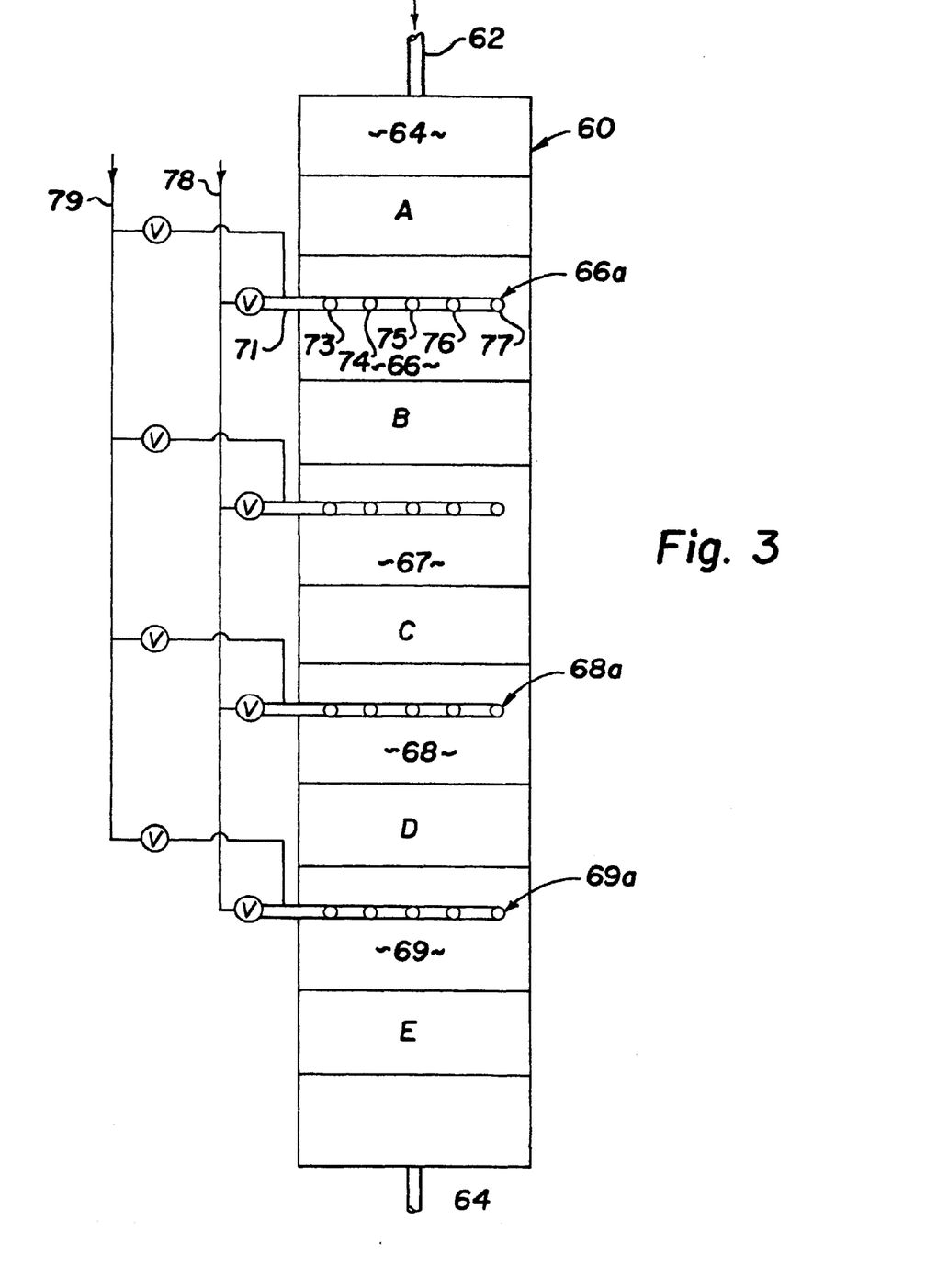
FIG. 3 is a side elevation, schematic illustration of an alkylation zone comprising a plurality of series-connected catalyst beds with the interstage injection of feed components in accordance with the present invention.

Turning now to FIG. 3, there is illustrated a preferred alkylation reactor 18 implementing the present invention through the use of sparger systems for the interstage injection of a quench fluid comprising usually mixtures of benzene and ethylene although either benzene or ethylene alone can also be employed in the quench fluid. The reactor 18 comprises an elongated reactive vessel 60 having an inlet 62 and an outlet 64. Benzene and ethylene are supplied to the reactor via inlet 62, and the alkylated product typically comprised of ethylbenzene and Sax polyethylbenzenes along with unreacted benzene and ethylene is withdrawn via line 64. The reactor comprises a plurality of series-connected catalyst beds A, B, C, D and E. Located above catalyst bed A is a plenum zone 63, and between the succeeding catalyst beds are intermediate mixing zones 66, 67, 68, and 69. Extending into the intermediate mixing zones are a plurality of sparger systems 66a through 69a. Each sparger system comprises a header tube or manifold 71 which extends transversely into the intermediate mixing zone as indicated in FIG. 3 and is shown in more detail in FIG. 4 described below. The header manifold supports a plurality of dispensing tubes 73, 74, 75, 76 and 77 which are spaced from one another in a generally horizontal or planar conformation. Each sparger system is supplied by ethylene through a supply line 78 and benzene through a supply line 79 through suitable proportioning valves as indicated to supply a quench fluid having the desired ratio of benzene and ethylene.

In at least the initial mixing zone, and preferably in the subsequent mixing zones as well, the sparger system is configured to provide the quench fluid comprising a mixture of the aromatic substrate and/or the ethylene into the mixing zone through a plurality of flow paths in which some flow paths are directed upwardly within the mixing zone and other flow paths directed downwardly within the mixing zone. In addition, the sparger system incorporating the dispersion tubes is located in the mixing zone in relative proximity to the overlying catalyst bed in order to further enhance mixing of the benzene and ethylene within the mixing zone. Stated differently, the header tube and the corresponding diffusion tubes are located within the upper half of the vertical dimension of the mixing zone and preferably within the upper ¼ of the mixing zone. Preferably, as described below, the flow paths through which quenching fluids are dispensed are oriented at acute angles from the horizontal within the range of 30° to 60° upwardly and downwardly. Preferably, the orifices are oriented at angles of about 45° from the horizontal of both upwardly and downwardly.

Figure 4:
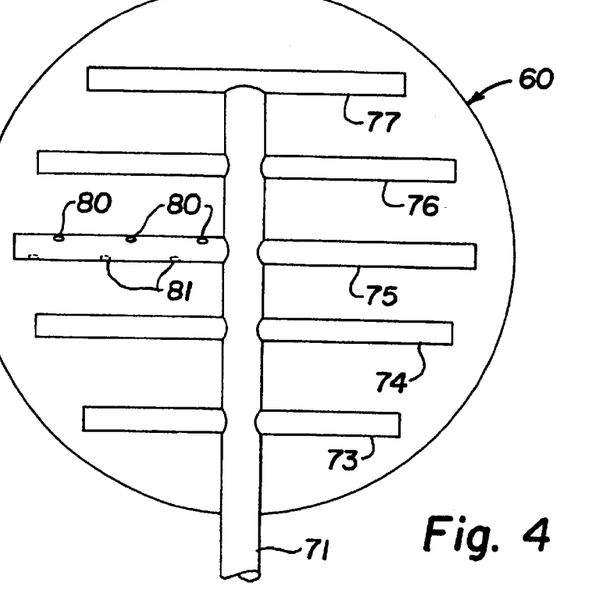
FIG. 4 is a plan view of a sparger system suitable for use in carrying out the present invention.
Figure 5:
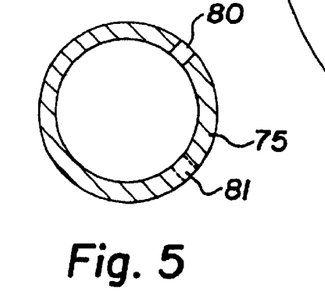
FIG. 5 is a idealized sectional view of a dispersion tube showing alternating arrangement of outlet orifices.

Turning now to FIG. 4, there is illustrated a preferred embodiment of the invention in which alternating upward and downward flow of the quenching fluid is accomplished through alternate orifices in a given dispersion tube. More specifically, FIG. 4 is a plan view of a sparger system incorporating a header tube 71 and dispersion tubes 73 through 77, with each dispersion tube equipped with alternating upwardly and downwardly oriented dispersion orifices. In FIG. 4, upwardly oriented orifices are indicated by solid lines and downwardly oriented orifices (which are masked when viewed from the top) are indicated by broken lines. Referring, for example, to the dispersion orifices shown in dispersion tube 75, orifices 80 are oriented in an upward direction and intervening orifices 81 are oriented in a downward direction. This sequential orientation of the alternating orifices is also shown in FIG. 4. The schematic offset sectional view of FIG. 5 shows orifice 80 oriented in an upward direction and orifice 81 oriented in a downward direction.

Figure 6:
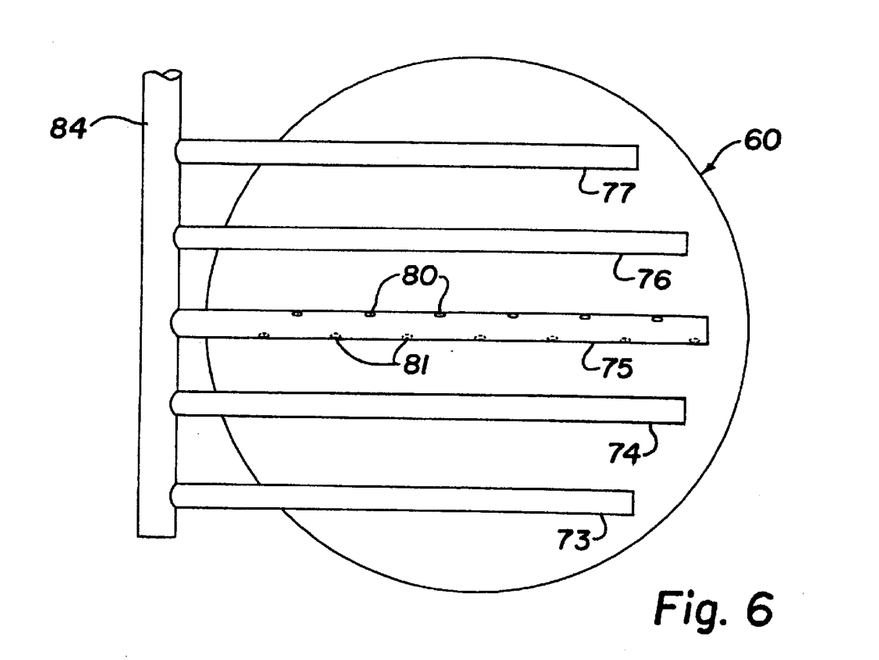
FIG. 6 is a plan view of a modified form of a sparger system employed in carrying out the present invention.

As can be seen from an examination of FIG. 3 and also FIG. 4, downward flow of feed stream from one catalyst to the next is influenced not only by the alternating dispersion of quench feed stock within the mixing zone but also by the presence of the header tube or manifold 71 extending into the mixing zone. FIG. 6 illustrates an alternative embodiment of the invention in which interference of the header tube with flow and mixing within the mixing zone is eliminated by placing the header manifold externally of the reactor.

In FIG. 6, the sparger system incorporates a plurality of dispersion tubes 73–77 similarly as described above with reference to FIGS. 3 and 4 and, in addition, an external manifolding system. In this embodiment of the invention, the dispersion tubes extend through the wall of the reactor 60 where they are connected to manifold 84 which provides an external header. Manifold 84 is connected to ethylene and benzene supply lines similarly as described above with reference to FIG. 3. In this embodiment of the invention, the mixing action of the alternating ports dispensing quench fluids from the dispersion tubes is maximized or enhanced since the header tube itself does not interfere with fluid flow through the mixing system.

Returning to FIG. 2, the effluent stream from one or both of the alkylation reactors 18 and 20 is supplied through a two-way, three-position outlet valve 24 and outlet line 25 to a two-stage benzene recovery zone which comprises as the first stage a prefractionation column 27. Column 27 is operated to provide a light overhead fraction including benzene which is supplied via line 28 to the input side of heater 14 where it is mixed with benzene in line 12 and then to the alkylation reactor input line 10. A heavier liquid fraction containing benzene, ethylbenzene and polyethylbenzene is supplied via line 30 to the second stage 32 of the benzene separation zone. Stages 27 and 32 may take the form of distillation columns of any suitable type, typically, columns having from about 20–60 trays. The overheads fraction from column 32 contains the remaining benzene which is recycled via line 34 to the alkylation reactor input. Thus, line 34 corresponds to the output line 4b of FIG. 1. The heavier bottoms fraction from column 32 is supplied via line 36 to a secondary separation zone 38 for the recovery of ethylbenzene. The overheads fraction from column 38 comprises relatively pure ethylbenzene which is supplied to storage or to any suitable product destination by way of line 40, corresponding generally to output line 4a of FIG. 1. By way of example, the ethylbenzene may be used as a feedstream to a styrene plant in which styrene is produced by the dehydrogenation of ethylbenzene. The bottoms fraction containing polyethylbenzenes, heavier aromatics such as cumene and butylbenzene, and normally only a small amount of ethylbenzene is supplied through line 41 to a tertiary polyethylbenzene separation zone 42. As described below, line 41 is provided with a proportioning valve 43 which can be used to divert a portion of the bottoms fraction directly to the transalkylation reactor. The bottoms fraction of column 42 comprises a residue which can be withdrawn from the process via line 44 for further use in any suitable manner. The overhead fraction from column 42 comprises a polyalkylated aromatic component containing diethylbenzene and triethylbenzene (usually in relatively small quantities) and a minor amount of ethylbenzene is supplied to an on stream transalkylation reaction zone. Similarly as described above with respect to the alkylation reactors, parallel transalkylation reactors 45 and 46 are provided through inlet and outlet connections involving valves 47 and 48. Both of reactors 45 and 46 can be placed on stream at the same time so that both are in service in a parallel mode of operation. Alternatively, only one transalkylation reactor can be on-stream with the other undergoing regeneration operation in order to burn coke off the catalyst beds. By minimizing the amount of ethylbenzene recovered from the bottom of column 38, the ethylbenzene content of the transalkylation feedstream can be kept small in order to drive the transalkylation reaction in the direction of ethylbenzene production. The polyethylbenzene fraction withdrawn overhead from column 42 is supplied through line 49 and mixed with benzene supplied via line 50. This mixture is then supplied to the on-line transalkylation reactor 45 via line 51. Preferably, the benzene feed supplied via line 50 is of relatively low water content, about 0.05 wt. % or less. Preferably, the water content is reduced to a level of about 0.02 wt. % or less and more preferably to no more than 0.01 wt. %. The transalkylation reactor is operated as described before in order to maintain the benzene and alkylated benzenes within the transalkylation reactor in the liquid phase. Typically, the alkylation reactor and the transalkylation reactor may be operated to provide an average temperature within the transalkylation reactor of about 150° F.–550° F. and an average pressure of about 600 psi. The preferred catalyst employed in the transalkylation reactor is zeolite Y having the characteristics described previously. The weight ratio of benzene to polyethylbenzene should be at least 1:1 and preferably is within the range of 1:1 to 4:1.

The output from the transalkylation reactor containing benzene, ethylbenzene and diminished amounts of polyethylbenzene is supplied via line 52 to the initial stage of the benzene recovery zone. This mode of operation is contrary to the normal mode of operation as disclosed in the aforementioned EPA 467,007 to Butler. As disclosed there, the output from the transalkylation reactor is supplied to the second stage of the benzene recovery zone, corresponding to column 32 in FIG. 2. While this mode of operation can be followed in carrying out the present invention, it is preferred to operate, as shown in FIG. 2, in which the transalkylation reactor output is supplied to the initial stage 27 of the benzene recovery zone. This offers the advantage of having a stream with approximately the same benzene and ethylbenzene composition as the stream from the alkylation reaction.

In the mode of operation described thus far, the entire bottoms fraction from the ethylbenzene separation column 38 is applied to the tertiary separation column 42 with overhead fractions from this zone then applied to the transalkylation reactor. This mode of operation offers the advantage of relatively long cycle lengths of the catalyst in the transalkylation reactor between regeneration of the catalyst to increase the catalyst activity. Another embodiment of the invention achieves this advantage by supplying a portion of the output from the ethylbenzene separation column through valve 43 directly to the transalkylation reactor. Surprisingly, by employing vapor phase alkylation coupled with liquid phase transalkylation in accordance with the present invention, a significant quantity of the bottoms fraction from the ethylbenzene column can be sent directly to the transalkylation reactor, thus decreasing the amount of residue which is lost from the process. This mode of operation is consistent with and particularly advantageous in combination with the operation of the alkylation reactor to retard transalkylation and enhance ethylbenzene production.

As shown in FIG. 2, a portion of the bottoms fraction from the secondary separation zone 38 bypasses column 42 and is supplied directly to the transalkylation reactor 45 via valve 43 and line 54. A second portion of the bottoms fraction from the ethylbenzene column is applied to the tertiary separation column 42 through valve 43 and line 55. The overhead fraction from column 42 is commingled with the bypass effluent in line 54 and the resulting mixture is fed to the transalkylation reactor via line 47. By bypassing the column 42 with a substantial portion of the bottoms product from column 38, the residue which is lost from the system can be reduced. Preferably in this mode of operation a substantial amount of the bottoms product from column 38 is sent directly to the transalkylation reactor, bypassing the polyethylbenzene column 42. Normally, the weight ratio of the first portion supplied via line 54 directly to the transalkylation reactor to the second portion supplied initially via line 55 to the polyethylbenzene would be within the range of about 1:2 to about 2:1. However, the relative amounts may vary more widely to be within the range of a weight ratio of the first portion to the second portion in a ratio of about 1:3 to 3:1.

Having described specific embodiments of the present invention, it will be understood that modifications thereof may be suggested to those skilled in the art, and it is intended to cover all such modifications as fall within the scope of the appended claims.

What is claimed:

1. A process for the alkylation of an aromatic substrate comprising:
   a. providing a multistage alkylation reaction zone having a plurality of series-connected catalyst beds each containing a molecular sieve aromatic alkylation catalyst, said catalyst beds being spaced from one another to provide intermediate mixing zones between adjacent-spaced catalyst beds;
   b. supplying a feedstock containing an aromatic substrate and a $C_2$–$C_4$ alkylating agent to an inlet side of said reaction zone;
   c. operating said reaction zone at temperature and pressure conditions in which said aromatic substrate is in the gaseous phase to cause gas phase alkylation of said aromatic substrate as said aromatic substrate and said alkylating progressively traverse said catalyst beds;
   d. in at least one intermediate mixing zone between adjacent catalyst beds, supplying a quench fluid comprising at least one of said aromatic substrate and said alkylating agent into the interior of said mixing zone through a plurality of flow paths in which one portion of said flow paths is directed upwardly within said mixing zone and another portion of said flow pats is directed downwardly within said mixing zone, wherein said quench fluid is supplied to said mixing zone trough a plurality of dispersion channels extend transversely within said mixing zone and spaced laterally from one another wherein at least some of said dispersion channels sense said quench fluid through said flow paths directed upwardly and downwardly within said mixing zone; and e. recovering alkylated product from a downstream outlet of said reaction zone.

2. The process of claim 1 wherein said aromatic substrate is benzene or a monoalkyl benzene.

3. The process of claim 1 wherein said aromatic substrate is benzene and said alkylating agent is an ethylating agent.

4. The method of claim 1 wherein said dispersion channels are located within the upper one-half of said mixing zone.

5. The method of claim 1 wherein said quench fluid is supplied at upward angles which are acute with respect to the horizontal and downward angles which are acute with respect to the horizontal.

6. The method of claim 5 wherein said upward and downward angles are acute angles within the range of 30–60°.

7. The method of claim 5 wherein said upwardly and downwardly acute angles are about 45° from the horizontal.

8. A process for the alkylation of an aromatic substrate comprising:

a. providing a multi-stage alkylation reaction zone within an elongated reactor having au upper catalyst bed extending transversely of said reactor and at least three subsequent catalyst beds extending transversely of said reactor and spaced from one another to provide an upper mixing zone between said first catalyst bed and the next subsequent catalyst bed, a second mixing zone between said second and third subsequent catalyst beds, and a third mixing zone between said third and fourth subsequent catalyst beds;

b. supplying a feedstock containing an aromatic substrate and a $C_2$–$C_4$ alkylating agent to an inlet side of said reaction zone;

c. operating said reaction zone at temperature and pressure conditions in which said aromatic substrate is in the gaseous phase to cause gas phase alkylation of said aromatic substrate as said aromatic substrate and said alkylating agent progressively traverse said catalyst beds;

d. in the initial intermediate mixing zone between said first and second catalyst beds, supplying a quench fluid comprising a mixture of said aromatic substrate and said alkylating agent into the interior of said mixing zone through a plurality of flow paths in which one portion of said flow paths is directed upwardly within said mixing zone and another portion of said flow pas is directed downwardly within said mixing zone, wherein said quench fluid is supplied to said mixing zone through a plurality of dispersion channels extending transversely within said mixing zone and spaced laterally from one another wherein at least some of said dispersion channels dispense said quench fluid through said flow paths dirt upwardly and downwardly within said mixing zone;

e. in at leapt one subsequent intermediate zone between adjacent catalyst beds, supplying a quench fluid comprising at least one of said aromatic substrate and said alkylating agent into the interior of sad mixing zone through a second plurality of flow paths in which one portion of said flow paths is directed upwardly within said mixing zone and another portion of said flow paths is directed downwardly wit said zone, wherein said quench fluid is supplied to said mixing zone through a plurality of dispersion channels extending transversely with said mixing zone and spaced laterally from one another wherein at least some of said dispersion channels dispense said quench fluid through said flow paths directed upwardly and downwardly within said mixing zone; and f. recovering alkylated product from a downstream outlet of said reaction zone.

9. The process of claim 8 wherein said aromatic substrate is benzene or a monoalkyl benzene.

10. The process of claim 8 wherein said aromatic substrate is benzene and said alkylating agent is an ethylating agent.

11. A process for the alkylation of an aromatic substrate comprising:

a. providing a multi-stage alkylation reaction zone within an elongated reactor having an upper catalyst bed extending transversely of said reactor and at least three subsequent catalyst beds extending transversely of said reactor and spaced from one another to provide an upper mixing zone between said first catalyst bed and the next subsequent catalyst bed, a second mixing zone between said second and third subsequent catalyst beds, and a third mixing zone between said third and fourth catalyst beds;

b. in each of said mixing zones, providing a sparger system comprising a plurality of laterally-spaced dispersion channels extending transversely of said reactor and provided with linearly-spaced outlet orifices alternately directed downwardly and upwardly along the lengths of said dispersion channels;

c. supplying a feedstock containing an aromatic substrate and a $C_2$–$C_4$ alkylating agent to an inlet side of said reaction zone;

d. operating said reaction zone at temperature and pressure conditions in which said aromatic substrate is in the gaseous phase to cause gas phase alkylation of said aromatic substrate as said aromatic substrate and said alkylating agent progressively traverse said catalyst beds;

e. in the initial intermediate mixing zone between said first and second catalyst beds, supplying a quench fluid comprising a mixture of said aromatic substrate and said alkylating agent to said sparger system to provide a plurality of alternating flow paths through said outlet orifices directed upwardly and downwardly within said mixing zone;

f. in the next intermediate mixing zone between said second and third catalyst beds, supplying a quench fluid comprising a mixture of said aromatic substrate and said alkylating agent to said sparger system to provide a plurality of alternating flow paths through said outlet orifices directed upwardly and downwardly within said mixing zone;

g. in the next intermediate mixing zone between said third and fourth catalyst beds, supplying a quench fluid comprising at least one of said aromatic substrate and said alkylating agent to said dispersion system to provide a plurality of alternating flow paths through said outlet orifices directed upwardly and downwardly within said mixing zone; and h. recovering alkylated product from a downstream outlet of said reaction zone.

12. The process of claim 11 wherein said aromatic substrate is benzene or a monoalkyl benzene.

13. The process of claim 12 wherein said aromatic substrate is benzene and said alkylating agent is an ethylating agent.

14. The process of claim 11 wherein in the initial mixing zone the sparger system incorporates said dispersion channels located in a generally planar conformation which is closer to the underside of the upper catalyst bed than to the top of the next subsequent catalyst bed.

15. The method of claim 14 wherein said quench fluid is supplied through said outlet orifices at upward angles which are acute with respect to the horizontal and at downward angles which are acute with respect to the horizontal.

16. The method of claim 15 wherein said upward and downward angles are acute angles within the range of 30–60°.

* * * * *

UNITED STATES PATENT AND TRADEMARK OFFICE
CERTIFICATE OF CORRECTION

PATENT NO.          : 6,486,371 B1
APPLICATION NO. : 09/723650
DATED                   : November 26, 2002
INVENTOR(S)        : James R. Butler and Denis Mignon It is certified that error appears in the above-identified patent and that said Letters Patent is hereby corrected as shown below:

In the Specification:

Column 8, line 65: replace "amounts. 7. Periodically," with --amounts. Periodically,--;

and

Column 9, line 35: replace "and Sax polyethylbenzenes" with --and polyethylbenzenes--.

In the Claims:

Column 13, line 5: replace"pats" with --paths--;

Column 13, line 7:  replace "trough" with --through--;

Column 13, line 8: replace "extend" with --extending--;

Column 13, line 11: replace "sense" with --dispense--;

Column13, line 35: replace "au" with --an--;

Column 13, line 59: replace "pas" with --paths--;

Column 14, line 4: replace "sad" with --said--;

Column 14, line 8: replace "wit said zone," with --within said mixing zone,--;

Column 14, line 11: replace "with" with --within--; and

UNITED STATES PATENT AND TRADEMARK OFFICE
CERTIFICATE OF CORRECTION

PATENT NO. : 6,486,371 B1
APPLICATION NO. : 09/723650
DATED : November 26, 2002
INVENTOR(S) : James R. Butler and Denis Mignon It is certified that error appears in the above-identified patent and that said Letters Patent is hereby corrected as shown below:

Column 14, line 34: replace "fourth catalyst" with --fourth subsequent catalyst--.

Signed and Sealed this

Third Day of October, 2006

JON W. DUDAS
*Director of the United States Patent and Trademark Office*